United States Patent [19]
Tsopelas et al.

[11] Patent Number: 6,112,576
[45] Date of Patent: Sep. 5, 2000

[54] GAS ANALYZER WITH BACKGROUND GAS COMPENSATION

[75] Inventors: S. Gregory Tsopelas, Brookline; Yufeng Huang, Southborough; Robert H Hammond, Cambridge, all of Mass.

[73] Assignee: Panametrics, Inc., Waltham, Mass.

[21] Appl. No.: 09/387,988

[22] Filed: Sep. 1, 1999

Related U.S. Application Data

[60] Provisional application No. 60/103,040, Oct. 5, 1998.
[51] Int. Cl.$^7$ .................................................. G01N 27/74
[52] U.S. Cl. .......................................... 73/25.02; 324/204
[58] Field of Search ............................ 73/25.02; 324/204

[56] References Cited

U.S. PATENT DOCUMENTS

| | | | |
|---|---|---|---|
| 4,893,495 | 1/1990 | Meyer | 73/25.02 |
| 5,012,669 | 5/1991 | Meyer | 73/25.02 |

*Primary Examiner*—Daniel S. Larkin
*Attorney, Agent, or Firm*—Nutter, McClennen & Fish, LLP

[57] ABSTRACT

A sensor responds to a magnetic wind produced by the magnetic susceptibility of a target component gas, such as oxygen, which is present together with a background gas in a sample located in a measurement field produced in a measurement device. A background sampler also determines thermal and physical characteristics in a conditioned flow path, and a processor performs a computational correction on the detected magnetic wind signal to more accurately determine the concentration of the target gas. The background sampler includes a mass flow cell in series with a laminar flow device to measure heat capacity and viscous properties of the sample. It derives the gas viscosity from a differential pressure measurement; and preferably determines the heat capacity and thermal conductivity of background gases, the composition of which may be unknown, to compensate for their effects on the magnetic wind sensor elements. A further correction for diamagnetism of the background is made using one or more correlations between the measured parameters in certain common gases or classes of gases. The determination of gas bulk properties allows the concentration of the target gas to be made with enhanced accuracy in the presence of unknown, unquantified or changing background components, and the necessary hardware may be used in conjunction with existing magnetic wind sensor and processor. In that case, the processor program is modified to apply the additional sensor inputs to correct the magnetic wind reading. A thermal conductivity correction is also made, and this may be directly derived from the bridge control signal when operating the magnetic wind sensors in mode to maintain constant temperature. The system may be used in petroleum tanks and hydrocarbon vent systems to monitor for explosive levels of oxygen.

10 Claims, 4 Drawing Sheets

GAS ANALYZER WITH BACKGROUND GAS COMPENSATION

CROSS-REFERENCE TO RELATED APPLICATION

This application is related to U.S. Provisional Patent Application Serial No. 60/103,040, filed Oct. 5, 1998 of which the priority is hereby claimed.

FIELD OF THE INVENTION

The present invention relates to instrumentation for measuring properties of fluids such as gases, and more particularly for measuring a property such as oxygen content, or for measuring such a property when varying or confounding material is present in the fluid which is to be measured. One class of oxygen-measuring sensors relies on detecting oxygen concentration by detecting wind- or force- created by the oxygen in a strong magnetic field or gradient, and resulting from the magnetic properties, specifically the paramagnetism, of the oxygen.

Gases are classified into two groups: paramagnetic gases and diamagnetic gases. Paramagnetic gases are those within which an applied magnetic field is slightly increased by the alignment of electron orbits. The permeability of paramagnetic materials is slightly greater than that of empty space. Diamagnetic gases are those within which an externally applied magnetic field is slightly reduced because of an alteration of the atomic electron orbits produced by the field. The permeability of diamagnetic materials is slightly less than that of empty space.

These magnetic properties of gases are measured in terms of susceptibility, i.e., the volume susceptibility K, where K is defined by $K=I/H$ where H is the intensity of an applied magnetic field, and I is the induced magnetic intensity acquired by the substance. Table I shows a list of volume magnetic susceptibility of common gases.

| Gas | Volume Susceptibility at 760 mmHg, 20° C. |
| --- | --- |
| Nitrogen | $-0.39 \times 10^{-9}$ |
| Oxygen | $141.3 \times 10^{-9}$ |
| Argon | $-0.748 \times 10^{-9}$ |
| Carbon Dioxide | $-0.78 \times 10^{-9}$ |
| Nitric Oxide | $60.3 \times 10^{-9}$ |
| Methane | $-1.67 \times 10^{-9}$ |
| Butane | $-2.38 \times 10^{-9}$ |

As shown in that table, most of these gases are diamagnetic except oxygen and nitric oxide, which are strongly paramagnetic. Volume susceptibility of gases decreases with increasing temperature. In a simple mixture, the presence and concentration of a certain gas can sometimes be detected by its unique magnetic susceptibility. For example, the high paramagnetic susceptibility of oxygen has allowed the design of a number of effective paramagnetic analyzers for detecting the concentration of oxygen in a sample gas. One typical design is a thermal paramagnetic analyzer, which combines magnetic field gradient and a temperature gradient within a measuring cell to cause a sample of an oxygen-containing mixture introduced into the cell to flow, creating a "magnetic wind", that is detected by a flow sensor. The intensity of this induced magnetic wind depends on the concentration of oxygen in the gas mixture. U.S. Pat. Nos. 5,012,669 and 4,893,495 show details of construction and methods of operating a sensing system of this type.

The mass flow rate of the magnetic wind is usually used as the indication of concentration of the target gas, e.g., oxygen, in the background mixture. This may be determined by reference to the outputs of a number of small thermal sensors located closely together inside the flow region. This approach allows measurement of oxygen concentration with reasonable accuracy under certain defined conditions. However, in practice, the target gas may be present in a background together with a number of other gases that vary in concentration over time, or that are themselves of complex or unknown composition and concentration. This may cause the concentration measurement to fluctuate in response to extraneous factors, even when the concentration itself remains constant. That is, the physical properties of the background gas affect the measurement. The mass flow rate measurement, is affected by the thermal characteristics and physical properties of the background gas, such as its heat capacity, viscosity, magnetic susceptibility and the like. Heat capacity is a measure of the thermal mass of the gas; the higher the heat capacity, the more mass flow. Viscosity is a measure of the flow friction the gas; the higher the viscosity, the slower the gas moves, decreasing the mass flow for a given driving force or gradient. The same concentration of the target gas in different background gases will therefore show different signals when detected by a thermal sensor responsive to heat exchange with the moving gas. Existing gas sensing analyzers are therefore only effective for measuring the concentration of the target gas in a well characterized or known, simple background gas.

However in many applications, the background gas is unknown, or is too complex to predict its thermal and physical properties.

Accordingly, it would be desirable to provide an improved sensor.

It would further be desirable to provide a sensing or measurement system that allows one to measure the concentration of a target gas present in a complex or unknown background gas.

It would further be desirable to provide a sensing or measurement system that corrects for, or identifies background gas.

SUMMARY OF THE INVENTION

This is achieved in accordance with one embodiment of the present invention by a device with a sensor that responds to a magnetic wind produced by paramagnetic or diamagnetic susceptibility of a target gas component, such as oxygen, that is present together with a background gas in a sample located in a measurement field produced by the device. The sample is placed in a conditioned flow path, and a background sampler determines thermal and physical characteristics of the sample. A processor applies these characteristics to compensate for effects on the sensor measurement due to the physical properties of the background gas mixture, performing a computational correction so as to more accurately determine the concentration of the target gas. This extends the utility of existing technologies in applications such as paramagnetic oxygen analyzers, which have been limited by the variability of their readings in the presence of extrinsic and uncontrolled background gas environments, and which hereto have performed measurements only in certain known background compositions that had been calibrated or modeled in advance.

The device employs a conditioned flow path with a mass flow cell to provide a reference thermal characteristic, and a laminar flow device in series with the mass flow cell to determine viscous properties of the sample. The device derives the gas viscosity from a differential pressure measurement across the laminar flow device, and determines from the mass flow measurement the heat capacity of background gases, the composition of which may be unknown, to compensate for the effects of the background gas on the magnetic wind sensing elements. Correction for the magnetic susceptibility of the background may also be done, relying on a relationship to the other (measured) parameters for certain classes of background gases. The determination of gas bulk properties allows the concentration of the target gas to be measured with enhanced accuracy in the presence of unknown or unquantified background gas components, and the necessary hardware may be used in conjunction with an existing magnetic wind sensor and processor. Preferably, the existing measurement system provides one of the desired thermal characteristic inputs at a specific temperature.

BRIEF DESCRIPTION OF THE DRAWINGS

These and other features of the invention will be understood from the following description of an illustrative embodiment and discussion of its operation, taken together with the drawings, wherein.

Figure 1:
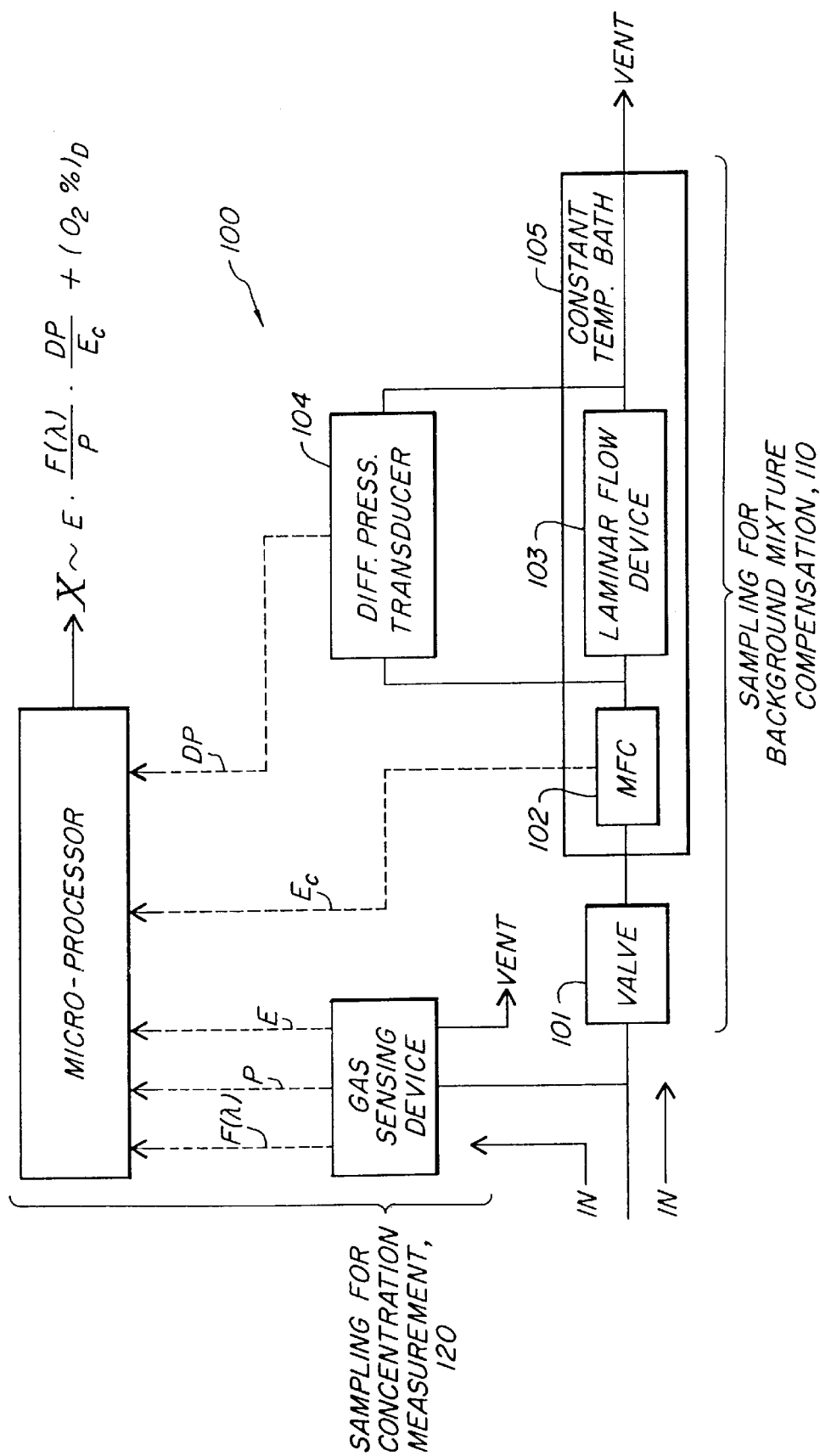
FIG. 1 is a block diagram of one embodiment of a measurement device of the present invention showing operative assemblies thereof.

The invention is best understood following a discussion of the theory of operation and several general design elements of a paramagnetic oxygen sensor operating on the magnetic wind principle. The magnetic wind sensor usually consists of two heated temperature-sensing elements or sets of elements, which are positioned with one located upstream of the other in the stream of a magnetic wind that is induced in a cell having precisely positioned thermal and magnetic fields. The magnetic wind cools the upstream sensor and warms the downstream one, and the difference in temperature between the two sensors is sensed by a bridge circuit as resistance changes in the two sensors. The voltage from the bridge is further amplified to produce a measurement signal output. When a magnetic wind is not present, a zero output is obtained since the two sensors then reside at the same temperature.

The intensity E of the magnetic wind produced in the gas-sensing device has the following form:

$$E = c_1 \cdot X \cdot P \cdot \frac{\rho \cdot C_p}{\mu} \quad (1)$$

where, E is the magnetic wind signal (in millivolts), X is the concentration of the target gas, P, $\rho$, $C_p$, and $\mu$ are pressure (in Pascals), density (in kg/m$^3$), specific heat (in J/kg·° K), and dynamic viscosity (in N·sec/m$^2$) of the gas mixture, respectively. The quantity $c_1$ is a constant that depends only on the gas-sensing device, while P, $\rho$, and $\mu$ are functions of gas temperature, and $C_p$ is almost independent of temperature for most common gases.

If magnetic wind flow sensor elements such as thermistors utilized in a gas analyzer have imminent contact with the gas mixture, they are sensitive to, and react differently to, variations in the thermal conductivity of the gas, because the conductivity affects the sensor's heat loss by heat conduction through flowing gas. A gas with large thermal conductivity tends to equalize the temperature gradient. In this case, the temperature difference between the upstream and downstream sensors is diminished in the presence of a flow. Equation (1) can be modified as follows to include the thermal conductivity effect of the gas:

$$E = c_1 \cdot X \cdot P \cdot \frac{\rho \cdot C_p}{\mu \cdot F(\lambda)} \quad (2)$$

where F is a linear function of thermal conductivity ($\lambda$) and is calibrated by the magnetic wind flow sensors. In equation (2), the thermal conductivity $\lambda$ of the gas mixture is a function of gas temperature.

From equation (2), it is obvious that the sensor output (E) is not only a function of the concentration of the target gas (X), but also a function of gas pressure and thermal physical properties $\rho C_p$, $\mu$, and $\lambda$ of the mixture. Because of this complicated functional dependence, it has conventionally been the case that the sensor output may be taken as a measurement of the target gas' concentration only when the gas mixture is known and is simple enough to predict their properties, or to have previously compiled the sensor operating characteristics therein.

However, applicant realized that certain relationships among the interaction of gas properties and the sensor behavior allow one to correct for the varying sensor output. In fact, by measuring several functions of the thermal and physical properties of the gas mixture at the same time, the sensor output (E) is fully compensated to provide a measure of the concentration of the target magnetically-responsive component (e.g., oxygen or nitric oxide).

This is done in a prototype embodiment of the invention by measuring the gas pressure, for example with an absolute pressure transducer; measuring the heat capacity ($\rho C_p$), for example using a thermal mass flow sensor; and measuring the viscosity, for example by sensing the pressure differential across a laminar flow device. In a preferred embodiment, the thermal conductivity is advantageously determined simply by operating the magnetic wind type sensors in a constant temperature mode as described in the above-referenced '495 patent, and applying the bridge voltage of the temperature feedback control in the gas sensing device as the thermal conductivity correction information.

When the heat capacity is measured in this fashion by a compensation mass flow sensor, (i.e., a sensor positioned in a well-quantified flow at known temperature) the sensor's output can be correlated as $$E_c = c_2 \cdot \rho \cdot C_p \cdot Q \quad (3)$$

where $E_c$ is the compensation sensor's output; Q (m$^3$/s) is the volumetric flow rate of the gas mixture and $c_2$ is a constant depending only on the sensor.

The gas viscosity of the sample is effectively ascertained by placing a differential pressure transducer across a laminar flow device, since viscosity is related to the pressure differential via the following relationship:

$$DP = c_3 \cdot Q \cdot \mu \quad (4)$$

Where $c_3$ is a constant depending only upon the laminar flow device. For example, if the laminar flow device is a segment of capillary tubing, $$c_3 = \frac{8 \cdot L}{\pi \cdot r^4} \quad (5)$$

where L and r are the length and radius of the capillary tube, respectively.

Equation (4) is valid only when the gas flow is in a laminar flow condition. The criterion of how to determine whether a flow is laminar or turbulent depends on the Reynolds number ($R_e$), which is defined by:

$$R_e = \frac{U \cdot D \cdot \rho}{\mu} \quad (6)$$

where U is the characteristic flow velocity, and D is the characteristic length of the device. For a capillary tube, the characteristic flow velocity is the mean flow velocity, and its characteristic length is the tube's diameter. If the Reynolds number is lower than a critical number ($Re_{cr}$), flow remains in laminar flow; if the Reynolds number is higher than the critical number, flow changes to turbulent. For a capillary tube, $Re_{cr}$ is about 2200. Thus, when measuring viscosity using a laminar flow device, the sampling flow rate has to be low enough so that its Reynolds number is smaller than $R_{ecr}$.

By laminar flow device applicant means a flow segment or piece of equipment that tends to maintain flow in laminar fashion and has a linear pressure drop across it as a function of volumetric flow rate. This contrasts, for example, to several common flow restrictors, such as an orifice, for which the pressure drop is highly nonlinear with flow, or such as a relatively short piece of sintered material, which may also be nonlinear. Suitable laminar flow devices are readily available from many instrumentation suppliers, and details of such a device require no further discussion.

The viscosity determined from the laminar flow may be used by plugging Equation (4) into Eq. (3), so Eq. (3) becomes:

$$\frac{E_c}{DP} = \frac{c_2}{c_3} \frac{\rho \cdot C_p}{\mu} \quad (7)$$

Thus, $E_c/DP$ is a true measurement of $\rho C_p/\mu$, and it is independent of the sample flow rate (Q).

By substituting equation (7) into Eq. (2), Eq. (2) becomes:

$$E = \left( \frac{c_1 \cdot c_3}{c_2} \cdot \frac{P}{F(\lambda)} \cdot \frac{E_c}{DP} \right) \cdot X \quad (8)$$

The gas pressure (P) may be compensated, i.e., accurately determined, by reference to an absolute pressure transducer, and its thermal conductivity can be compensated by reference to the bridge voltage in a constant sensor temperature magnetic wind gas-sensing device as described above. Thus, Equation (8) provides a measurement of the concentration (X) of the target gas, which is independent of, or corrected for the effects of, the background gas mixture.

The present invention uses a mass flow, controller, a laminar flow device and a differential pressure transducer to compensate heat capacity and viscosity's effect of background mixture. Gas pressure is compensated by an absolute pressure sensor, and gas thermal conductivity is compensated by bridge voltage of sensing device. In addition, as described further below in connection with FIGS. 3 and 4, the processor preferably also corrects the measurement for variations introduced by magnetic susceptibility of the background gas.

Figure 2:
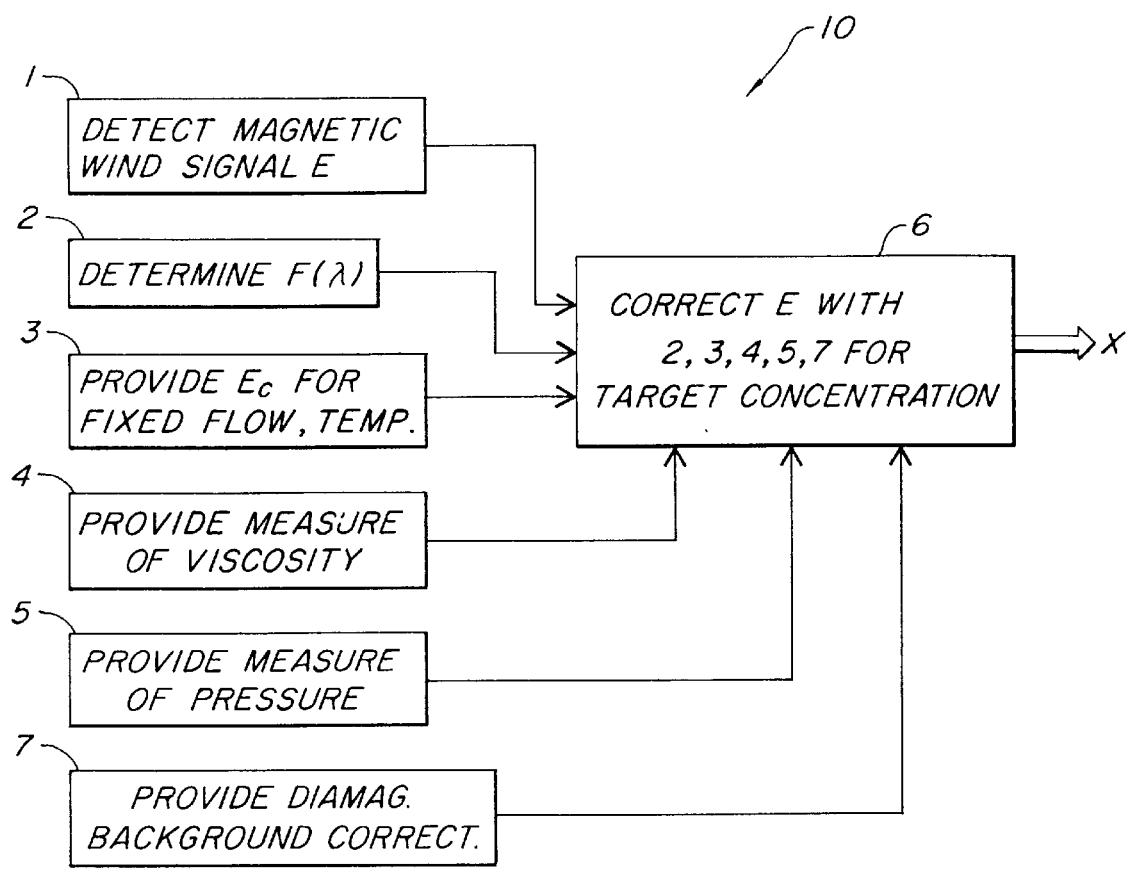
FIG. 2 is a chart of processing steps useful in operation of the device of FIG. 1.

FIG. 2 illustrates the steps of the method 10 of the present invention for measuring the concentration of a target gas by the magnetic wind technique. The method includes the first step 1 of detecting the intensity of the magnetic wind in a suitable measurement cell, such as a thermo-magnetic cell of conventional type. The cell may be operated with a sensor control loop that maintains a constant temperature, providing a bridge voltage that gives a measure 2 of the thermal conductivity correction $F(\lambda)$. These data are provided to a microprocessor for conversion to the target gas concentration. In parallel with that measurement, another measurement 3 is taken on the sample gas stream to determine a wind compensation measurement $E_c$ of the sensor response in a fixed temperature and flow, and a third correction factor is provided at step 4 by a viscosity-indicating measurement, which, as noted above is advantageously made by taking the pressure drop along a laminar flow path, and a fourth correction 5 is provided by an absolute pressure measurement. The data for the thermal conductivity correction 2 and the three measures 3,4,5 are provided to the microprocessor to correct the magnetic wind reading to a value that is directly proportional to the target gas concentration, so that the final computation 6 accurately indicates the concentration despite unknown or varying background. As described further in connection with FIGS. 3 and 4 below, the processor may also compute a correction due to the magnetic susceptibility of the background gas in a further step 7, using data from the same sensing assemblies.

FIG. 1 is a schematic diagram of the hardware elements of a preferred embodiment 100 of the present invention. This embodiment includes a mass flow controller 102 with a compensation sensor (not shown), and a laminar flow device 103 and differential pressure transducer 104, to correct the effects or measurement artifacts of the heat capacity and viscosity of the unknown background mixture. The gas pressure is corrected by reference to an absolute pressure sensor, and the thermal conductivity of the gas is compensated by the bridge voltage of a magnetic wind sensing device.

The architecture of that system 100 employs a sample conditioning assembly (not shown) which may be of conventional type, that conditions the sample of a flue, vent or process gas stream or the like, and passes it as an inlet stream, to the measurement system 100. The inlet stream passes in parallel to a sensing device 120, such as the paramagnetic oxygen sensor of the aforesaid '495 patent, and to a background correction system 110 which develops the viscosity and heat capacity measurements described above and provides them to the microprocessor of the device 120 to effect its compensation processing in accordance with the correction relations described above.

As shown in FIG. 1, the sampling system for background gas compensation receives a controlled sample through valve 101 which passes to the mass flow controller 102 where a sensor located in the controlled flow provides the compensation signal $E_c$ to the processor for correcting the gas heat capacity. A low flow range mass flow controller (MFC) of about ~40–50 sccm nitrogen equivalent flow is preferred as a way of measuring and controlling mass flow. The upstream valve 101 is used to adjust upstream pressure to a level appropriate for the flow controller.

The laminar flow device 103 or capillary tube is connected in series to the mass flow controller and both are preferably maintained in a constant temperature or temperature-controlled bath 105. The differential pressure transducer 104 measures the pressure drop DP across the capillary tube, which in accordance with Eq. (4), is indicative of the viscosity. This output is combined with the output $E_c$ from the mass flow sensor to correct the magnetic wind sensor output of Eq. (2) in accordance with the thermal conductivity and absolute pressure measurement.

The signal output (E) from the gas sensing device and the compensation signals ($E_c$ and DP) are provided to the control microprocessor, which executes a suitable computational program for correcting the former by the ratio of the latter to output a fully compensated magnetic wind value representative of the target gas concentration.

Advantageously, the additional background sensing elements of the described embodiment can be installed quite flexibly in relation to the magnetic wind sensing elements, since the magnetic and thermal fields of the wind sensor are not needed for the additional thermal and viscosity determinations. It is only necessary that the sample being tested for thermal and viscous characteristics be substantially the same as that being monitored in the paramagnetic sensing instrument. For this reason the two paths are preferably parallel branches at the valve 101. In a preferred embodiment, the background sampler 110 is an external stand-alone unit. It may thus be attached on an as-needed basis, to take its additional measurements and provide these as additional input signals to the microprocessor only when the paramagnetic sensing unit is to be used in an exotic or undetermined background environment, or in a background which is known to substantially affect the output, or when an enhanced level of accuracy is required. For example this module may be added to an existing measurement device to obtain more exact oxygen measurements in the presence of hydrocarbon fumes for anti-explosion monitoring, or to detect nitric oxide in the presence of process fumes for health monitoring. Alternatively, in other embodiments, the elements of the background gas property subsystem 110 may be installed in series to, or internally integrated into that thermo-magnetic gas sensing instrument 120, although this would involve somewhat greater design complexity and a higher base system cost.

It should be noted that viscosity is a strong function of temperature, and the mass flow controller usually has a temperature coefficient of about 0.1% F.S./° C. Thus, if the gas sensing system is to be installed outdoors, a 20° C. change from daytime to night could be expected to contribute up to 2% of full scale error if the flow cell is not in a temperature-stabilized environment. Thus, temperature stabilization is preferred, especially when large thermal variations are to be encountered.

In addition to the above thermal and flow characteristics, the measurement of the target gas in a gas mixture is also affected by the magnetic susceptibility of the background gas. For example, pure butane has a diamagnetic susceptibility which is equivalent to −1.3% of oxygen. So, 2% of oxygen in butane will give an indication of the presence of only 0.7% of oxygen. The other 1.3% of signal is offset by the background gas' diamagnetic susceptibility. If the error from background gas' diamagnetic effect is considered, equation (8) should be modified to $$E = \left(\frac{c_1 \cdot c_3}{c_2} \cdot \frac{P}{F(\lambda)} \cdot \frac{E_c}{DP}\right) \cdot (X - (O_2\%)_D), \quad (9)$$

where $(O_2\%)_D$ is the oxygen equivalent diamagnetic percentage. In accordance with a further aspect of a preferred embodiment of the invention, the processor utilizes the magnetic susceptibility of the background gas (or $(O_2\%)_D$) to fully and accurately correct the measure of oxygen concentration in the background gas.

Figure 3:
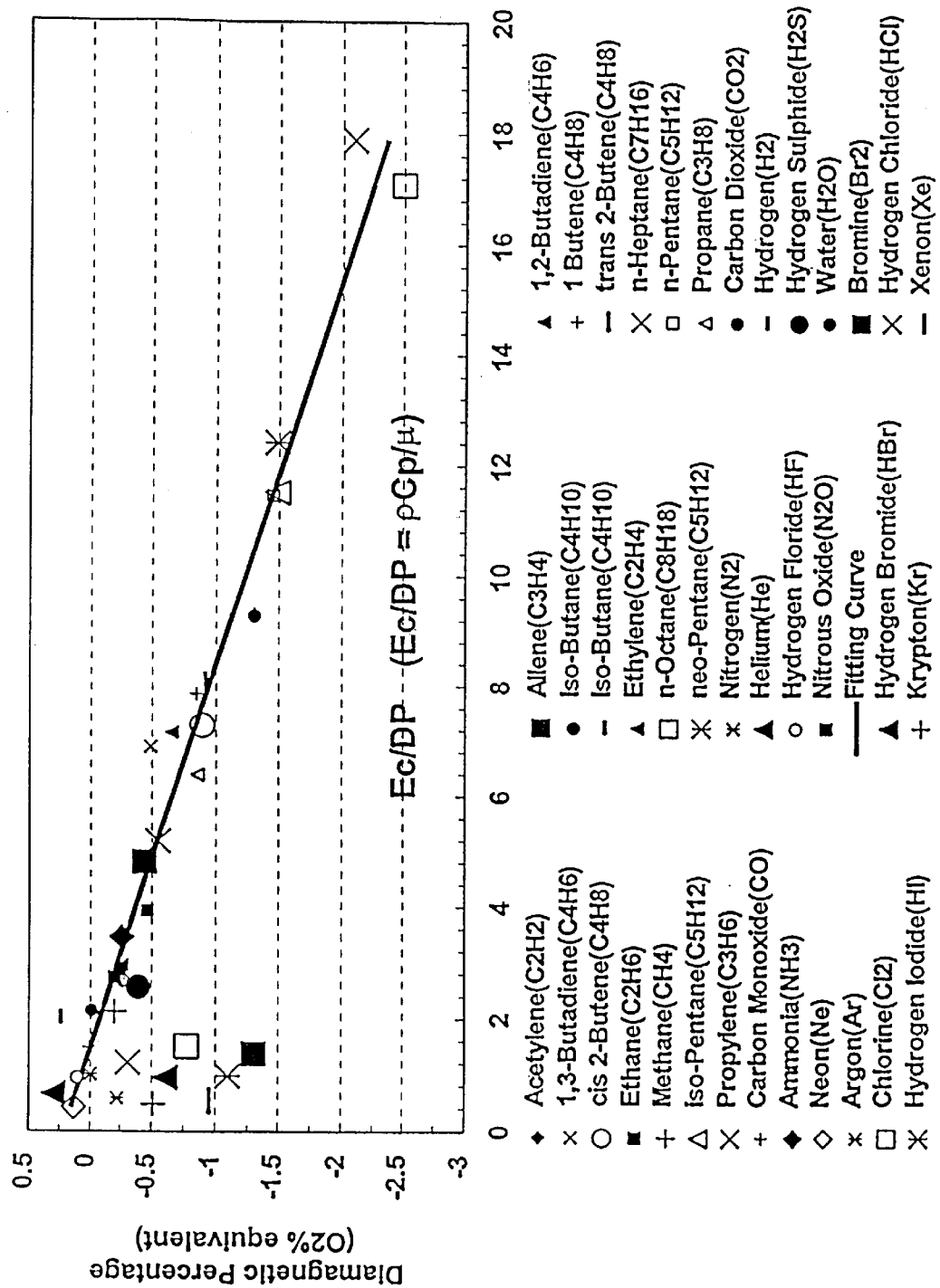
FIG. 3 is a chart of diamagnetic percentage as a function of measured sample parameters for a number of background gases.

The diamagnetic susceptibility of a gas may be related to its heat capacity, viscosity, and thermal conductivity via $$(O_2\%)_D = G\left(\frac{\rho \cdot C_p}{\mu}, \lambda\right) = G\left(\frac{E_c}{DP}, \lambda\right), \quad (10)$$

where G is a certain function. For hydrocarbons and most of the commonly encountered non-hydrocarbon gases, $(O_2\%)_D$ is found to be a strong function of $\rho C_p/\mu$ only. FIG. 3 plots this function for a number of these gases. A linear correlation between $(O_2\%)_D$ and $\rho C_p/\mu$ $$\left(\text{or } \frac{E_c}{DP}\right)$$

shows a good fit. In this case, diamagnetic susceptibility of background gas can be corrected by taking the measured values for $$\frac{E_c}{DP},$$

and simply correcting the measurement of Eq. 9.

Figure 4:
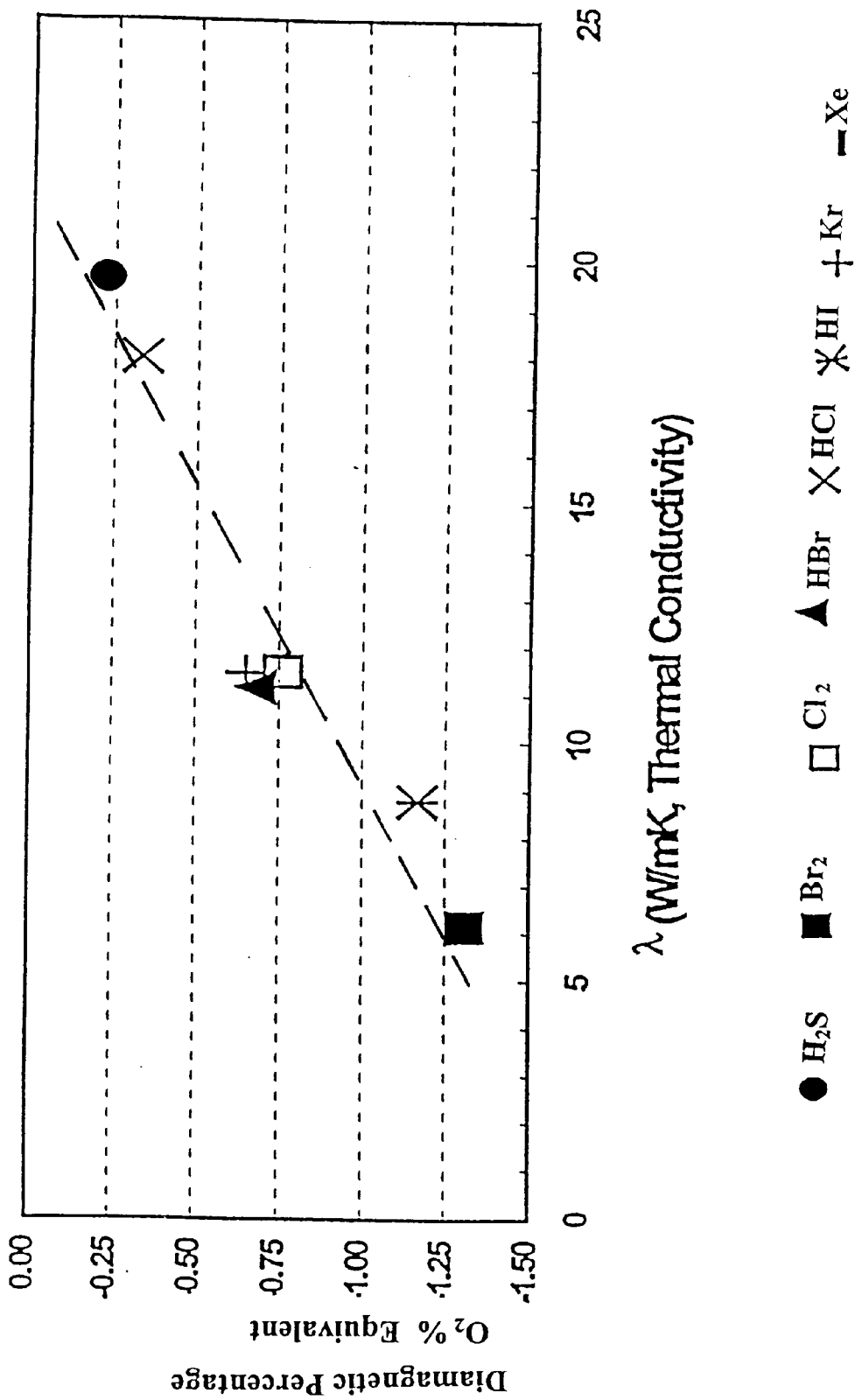
FIG. 4 show correlation between diamagnetic percentage and thermal conductivity for special gases.

For other special gases, such as chlorine, hydrogen chlorine, and bromine, their diamagnetic susceptibility can be compensated by their thermal conductivity. FIG. 4 shows the correlation of these gases' diamagnetic susceptibility with their thermal conductivity values. Clearly, as thermal conductivity decreases, the corresponding diamagnetic susceptibility is stronger. For these gases, $(O_2\%)_D$ can be compensated by utilizing thermal conductivity measurements. As a practical matter, the diagmagnetic compensation of FIG. 3 and that of FIG. 4 may both be applied simultaneously. This is because, on the one hand, the use of $E_c$/DP (FIG. 3) for diamagnetic compensation does not affect those special gases since the curve in FIG. 3 gives a near-zero correction for those gases. On the other hand, the use of thermal conductivity (FIG. 4) for diamagnetic compensation does not affect hydrocarbons, since the curve in FIG. 4 gives a near-zero correction for hydrocarbons and most other common gases.

The invention being thus disclosed and representative embodiments described together with the theory of operation, further variations and modifications will occur to those skilled in the art, and all such variations and modifications are considered to be within the spirit and scope of the invention, as set forth and defined by the claims appended hereto and their equivalents.

What is claimed is:

1. A system for measuring the amount of a target component gas which is present together with a background gas in a sample, such system comprising:

a magnetic wind sensor including at least one sensing element positioned in a measurement cell to respond to magnetic wind of the sample and produce a sensor response indicative thereof, a background sampler which receives at least a portion of the sample and produces an output indicative of thermal and physical characteristics of the sample, wherein said thermal and physical characteristics vary with background gas, and a processor, said processor applying said background sampler output to correct sensor response to the background gas and thereby determine concentration of the target component in the presence of said background gas.

2. The system of claim 1, wherein the background sampler includes a thermal mass flow cell, and wherein said sampler determines heat capacity from a thermal mass flow measurement.

3. The system of claim 1, wherein said background sampler includes a differential pressure sensor, and wherein the sampler determines viscosity from pressure differential measurement across a laminar flow device.

4. The system of claim 3, wherein said background sampler maintains said laminar flow device at a fixed temperature.

5. The system of claim 1, wherein said background sampler comprises a mass flow cell maintained at a fixed temperature for providing a thermal coefficient correction due to ambient change.

6. The system of claim 1, wherein said background sampler comprises a mass flow cell maintained at a fixed temperature for providing a thermal coefficient correction due to ambient change, and a laminar flow segment in series with the mass flow cell for developing a pressure drop representative of gas viscosity.

7. The system of claim 1, further comprising a feedback control loop for driving said magnetic wind sensor at constant temperature, and wherein the processor applies a bridge voltage of said feedback loop to correct thermal conductivity effects of the background gas.

8. The system of claim 1, wherein the processor applies a computational correction for diamagnetic properties of the background gas.

9. The system of claim 8, wherein the processor determines a diagmagnetic correction as an empirical correlation of diamagnetism with at least one of a thermal or flow property of the sample.

10. A method of measuring concentration of a target gas having a characteristic magnetic susceptibility when the target gas is present together with background gas in a sample, such method comprising the steps of:

providing the sample to a measurement cell having thermal and magnetic fields to generate a magnetic wind and sensing the magnetic wind to provide a first output representative thereof, providing the sample to a conditioned flow cell and developing a second output representative of thermal and physical characteristics of the sample, and compensating the first output by the second output to determine the concentration of the target gas in the sample.

* * * * *